US00PP18792P2

(12) United States Plant Patent
van Rijn

(10) Patent No.: US PP18,792 P2
(45) Date of Patent: May 6, 2008

(54) ***ANTHURIUM* PLANT NAMED 'RIJN200023'**

(50) Latin Name: *Anthurium andreanum*
Varietal Denomination: RIJN200023

(75) Inventor: Leonardus W. B. M. van Rijn, De Lier (NL)

(73) Assignee: Rijnplant BV, De Lier (NL)

( * ) Notice: Subject to any disclaimer, the term of this patent is extended or adjusted under 35 U.S.C. 154(b) by 0 days.

(21) Appl. No.: 11/540,401

(22) Filed: Sep. 30, 2006

(51) Int. Cl.
*A01H 5/00* (2006.01)

(52) U.S. Cl. ..... Plt./365

(58) Field of Classification Search ..... Plt./365
See application file for complete search history.

(56) References Cited

PUBLICATIONS

GTITM UPOVROM Citation for 'RIJN200023' as per QZ PBR 20040984; May 27, 2004.*

* cited by examiner

*Primary Examiner*—Kent Bell

(57) ABSTRACT

A new cultivar of *Anthurium* plant named 'RIJN200023' that is characterized by an upright and outwardly spreading habit, dark green leaves, freely spathing, red spathes positioned above the foliage on strong erect scapes, long spathe life, large spathe size and white and yellow colored spadices.

1 Drawing Sheet

Botanical classification: *Anthurium andreanum.*
Variety denomination: 'RIJN200023'.

BACKGROUND OF THE INVENTION

The present invention relates to a new and distinct cultivar of *Anthurium* plant botanically known as *Anthurium andreanum* and hereinafter referred to by the cultivar name 'RIJN200023'.

'RIJN200023' is a hybrid that originated from the hybridization of the female or seed parent a proprietary *Anthurium* identified as 9821 (not patented) and the male or pollen parent a proprietary *Anthurium* identified as 9613 (not patented). The cultivar 'RIJN200023' was selected by the inventor in May of 2000 as a single plant within the progeny of the stated cross in De Lier, The Netherlands.

Asexual reproduction by tissue culture of the new cultivar 'RIJN200023' was first performed in July of 2000 in Melsen-Merelbeke, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Anthurium* cultivar 'RIJN200023'.

1. *Anthurium* 'RIJN200023' exhibits an upright and outwardly spreading habit.
2. *Anthurium* 'RIJN200023' exhibits dark green leaves.
3. *Anthurium* 'RIJN200023' exhibits free flowering.
4. *Anthurium* 'RIJN200023' exhibits red spathes positioned above the foliage on strong erect scapes.
5. *Anthurium* 'RIJN200023' exhibits long spathe life.
6. *Anthurium* 'RIJN200023' exhibits a large spathe size.
7. *Anthurium* 'RIJN200023' exhibits white and yellow colored spadices.

The closest comparison cultivar is *Anthurium* 'Red Queen' (not patented). The new cultivar 'RIJN200023' is distinguishable from 'Red Queen' by the following characteristics:

1. 'RIJN200023' has spathes that are brighter red than 'Red Queen'.
2. 'RIJN200023' has larger spathes than 'Red Queen'.
3. 'RIJN200023' has spathes that are more heart shaped than 'Red Queen'.
4. 'RIJN200023' has foliage that is more durable than 'Red Queen'.

The new cultivar 'RIJN200023' is distinguishable from the male parent *Anthurium* 9613 in having larger leaves.

The new cultivar 'RIJN200023' is distinguishable from the female parent *Anthurium* 9821 in having wider leaves and darker spathes.

BRIEF DESCRIPTION OF THE DRAWING

The accompanying photograph illustrates the distinguishing traits of *Anthurium* 'RIJN200023'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Anthurium* cultivar named 'RIJN200023'. Data was collected in De Lier, The Netherlands from 12 month old greenhouse grown plants in 21 cm containers. The time of year was Summer and the average temperature was 23 degrees Centigrade during the day and 21 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'RIJN200023' has not been tested under all possible conditions and phenotypic differences may be observed with variations in environmental, climatic, and cultural conditions, however, without any variance in genotype.

Botanical classification: *Anthurium andreanum* 'RIJN200023'.
Use: Ornamental.
Parentage: 'RIJN200023' is a hybrid plant that resulted from the hybridization of the following parent plants:
*Female parent.*—A proprietary *Anthurium* identified as 9821.
*Male parent.*—A proprietary *Anthurium* identified as 9613.
Vigor: Moderate.
Growth rate: Moderate.
Growth habit: Moderately branching from base, bushy and dense.
Plant shape: Inverted triangle with inflorescences on top.
Suitable container size: 14 cm diameter container.
Height: Average 66.5 cm to top of leaf plane, 74 cm to top of inflorescences.
Width: Average 74 cm. in width.
Hardiness: USDA Zone 10.
Propagation: Tissue Culture.
Time to initiate roots (summer and winter): Approximately 28 days to produce roots on an initial cutting.
Time to produce a rooted cutting or liner (summer and winter): Approximately 270 days.
Root system: Fine and fibrous.
Stem:
*Average number of stems.*—4.
*Stem appearance.*—Stems very short.
*Stem length.*—2.2 cm.
*Stem diameter.*—1.8 cm.
*Internode length.*—1 mm.
*Stem aspect.*—Glabrous.
*Stem strength.*—Strong.
*Stem color* (*immature*).—145C to 145D.
*Stem color* (*mature*).—145B to 145C.
Foliage:
*Texture.*—Smooth.
*Leaf arrangement.*—Alternate.
*Compound or single.*—Single.
*Leaf shape.*—Narrow cordate.
*Leaf apex.*—Apiculate.
*Leaf base.*—Cordate.
*Leaf length.*—Average 29.8 cm in length.
*Leaf width.*—17.5 cm in width.
*Quantity of leaves per clump.*—Average 4.
*Pubescence.*—Absent.
*Leaf margin.*—Entire.
*Vein pattern.*—Pinnate.
*Young leaf color* (*upper surface*).—141A to 147A.
*Young leaf color* (*lower surface*).—146A.
*Mature leaf color* (*upper surface*).—139A to 147A.
*Mature leaf color* (*lower surface*).—144A to 146A.
*Vein color* (*lower surface*).—144C.
*Vein color* (*upper surface*).—144A.
*Leaf attachment.*—Petiolate.
*Petiole dimensions.*—Average 44.5 cm in length excluding geniculum, 4 mm in diameter below geniculum to 7 mm in diameter above clump.
*Petiole aspect.*—Round.
*Petiole color.*—144A.
*Geniculum dimensions.*—Average 3.3 cm in length and 6 mm in diameter.
*Geniculum aspect.*—Rounded, slightly glossy, glabrous.
*Geniculum color.*—144A to 144B.
*Wing length.*—5.1 cm.
*Wing diameter.*—6 mm.
*Wing color.*—144A to 144B, margins 146D.
*Durability of foliage to stress.*—High.
Inflorescence:
*Inflorescence arrangement.*—Spathes with spadices held above and beyond the foliage, flowering structures arise from leaf-axils.
*Flowering habit.*—Continuous.
*Quantity of spathes per plant.*—Average 8.
*Natural flowering season.*—Autumn.
*Time to flower or response time.*—8 months.
*Fragrance.*—Absent.
*Longevity.*—3 months in summer, 2 months in winter.
*Self-cleaning or persistent.*—Persistent.
*Spathe aspect.*—Cupped.
*Spathe arrangement.*—5° from vertical.
*Spathe dimensions.*—Average 14.9 cm in length, 11.8 cm in width.
*Spathe texture.*—Glabrous, slightly leathery.
*Spathe shape.*—Reniform to broad cordate.
*Spathe margin.*—Entire.
*Spathe apex.*—Abruptly acute.
*Spathe color when opening* (*front side*).—46B.
*Spathe color when opening* (*back side*).—47A to 42B; apex 46B to 46C.
*Spathe color when fully opened* (*front side*).—45B to 46B.
*Spathe color when fully opened* (*back side*).—N34A; apex 45A to 45B.
*Spathe color fading to.*—N34A; base 143A.
*Spathe longevity.*—During summer 3 months; during winter 2 months.
*Spadix arrangement.*—5° from vertical.
*Spadix shape.*—Columnar.
*Spadix tip.*—Obtuse.
*Spadix base.*—Obtuse.
*Spadix dimensions.*—Average 8.4 cm in length and 1 cm in diameter.
*Spadix color when opening.*—155A, apex 22A.
*Spadix color when fully opened.*—155A, apex 21A to 21B.
*Quantity of flowers per spadix.*—Average 400.
*Spadix flower arrangement.*—Bisexual, rounded in cross-section, single.
*Spadix flower dimensions.*—2 mm in diameter and less than 0.5 mm in depth.
Reproductive organs:
*Anther color.*—155B.
*Amount of pollen.*—Very low.
*Pollen color.*—155B.
*Stigma color.*—155D.
*Ovary color.*—155D.
Peduncle:
*Peduncle dimensions.*—Average 55.6 cm in length and 5 mm in diameter.
*Peduncle angle.*—5° from vertical.
*Peduncle color.*—144A.
*Peduncle strength.*—Strong.
Seed: Seed production has not been observed.
Disease and insect resistance: Plants of the new *Anthurium* have not been observed for disease or insect resistance.

It is claimed:

1. A new and distinct variety of *Anthurium* plant named 'RIJN200023' as described and illustrated.

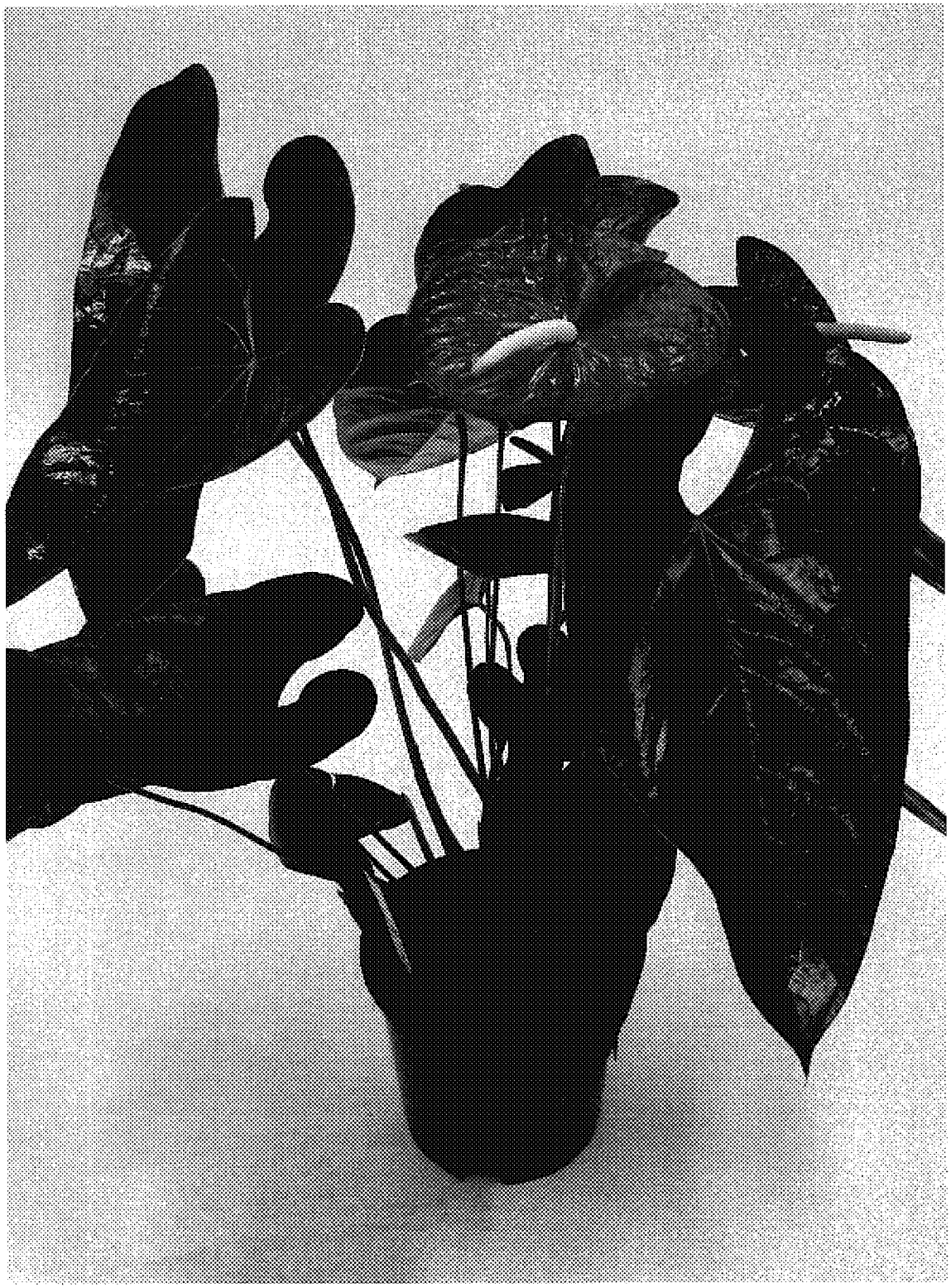

* * * * *